US006221108B1

(12) United States Patent
Smith

(10) Patent No.: US 6,221,108 B1
(45) Date of Patent: Apr. 24, 2001

(54) PROCESS FOR IMPROVING THE FRICTION RATE OF SOFT/COMPLIANT POLYURETHANES

(75) Inventor: Nigel Smith, Wokingham (GB)

(73) Assignee: Howmedica International Inc. (IE)

( * ) Notice: Subject to any disclaimer, the term of this patent is extended or adjusted under 35 U.S.C. 154(b) by 0 days.

(21) Appl. No.: 09/071,564

(22) Filed: May 1, 1998

(30) Foreign Application Priority Data

May 2, 1997 (GB) .................................................. 9709072

(51) Int. Cl.$^7$ ........................................................ A61F 2/28
(52) U.S. Cl. ............................................................ 623/16.11
(58) Field of Search ................................ 623/16, 18, 22, 623/23, 16.11, 18.11, 19.11, 19.12, 20.14, 22.11, 22.15

(56) References Cited

U.S. PATENT DOCUMENTS

| | | | |
|---|---|---|---|
| 4,888,024 | * 12/1989 | Powlan | 623/23 X |
| 5,047,054 | * 9/1991 | Vijayan et al. | 623/16 |
| 5,067,964 | * 11/1991 | Richmond et al. | 623/18 X |
| 5,593,452 | * 1/1997 | Higham et al. | 623/23 |
| 5,759,205 | * 7/1998 | Valentini | 623/16 |
| 5,879,404 | * 3/1999 | Bateman et al. | 623/22 X |

OTHER PUBLICATIONS

J. Blamey et al.: "Soft Layered Prosthesis For Arthritic Hip Joints: A Study of Materials Degradation". Journal of Biomedical Engineering, vol. 13, No. 1, Jan., 1991 (1991–01), pp. 180–184, XP000863669.*

F. Quigley et al.: "The Dynamic Mechanical Behaviour of Selected Medical Grade Polyurethanes" Key Engineering Materials, vol. 118–119, pp. 313–320. XP000863670 CH. The whole document.

J. Blamey et al.: "Soft Layered Prosthesis For Arthritic Hip Joints: A Study of Materials Degradation" Journal of Biomedical Engineering, vol. 13, No. 1, Jan., 1991 (1991–01), pp. 180–184, XP000863669. The whole document.

Habal, Muntaz B. et al.: New Finger Joint 1–6 Implantable Prosthesis in an Ex–vivo Model: Biostereometric Studies Polymeric Materials Science and Engineering, vol. 53, 1985, pp. 775–777, XP0000863672. The whole document.

McCarthy S J et al.: "In–vivo degradation of polyurethanes: transmission—FTIR microscopic characterization of polyurethanes sectioned by cryomicrotomy" Biomaterials, GB Elsevier Science Publishers BV., Barking, vol. 18, No. 21, pp. 1387–1409. XP00402619, ISSN: 0142–9612. Abstract.

* cited by examiner

*Primary Examiner*—Michael J. Milano
*Assistant Examiner*—Hieu Phan
(74) *Attorney, Agent, or Firm*—Lerner, David, Littenberg, Krumholz & Mentlik, LLP

(57) ABSTRACT

A process for improving the start up and steady rate friction of soft/compliant polyurethane bearings uses a pre-treatment with Ringers solution. The process includes treating the polyurethane in a heated bath of the solution for 96 hours at a temperature of between 30° C. and 37° C.

17 Claims, 5 Drawing Sheets

PROCESS FOR IMPROVING THE FRICTION RATE OF SOFT/COMPLIANT POLYURETHANES

BACKGROUND OF THE INVENTION

1. Field of the Invention

This invention relates to a process for improving start up and steady rate friction of soft/compliant polyurethanes and to polyurethane elements which have been treated by the process. An important potential application for such treated material is in compliant layer bearings, for example, those used in artificial joint replacements, although it also has other applications.

2. Description of the Prior Art

Typically these artificial joint replacement bearings are relatively recent and rely on the use of soft/compliant polyurethanes (or other elastomeric materials) to improve the lubrication mechanism compared with convention artificial joints. The concept of using a compliant polyurethane layer on the bearing surface of an artificial joint replacement is inspired by the natural synovial joint which has such a compliant layer, the articular cartilage. A combination of lubrication mechanisms have been proposed for synovial joints which result in fluid film lubrication, where the joint surfaces are completely separated by a thin film of lubricant. Currently most artificial joints are based upon metal on ultra high molecular weight polyethylene (UHMWPE), ceramic on UHMWPE or metal on metal material couples. These bearings are far less compliant than the natural joint and hence operate in a mixed lubrication regime, with partial contact of the two bearing surfaces. This leads to higher friction, and wear of the bearing surfaces of conventional joints. In contrast, compliant bearings operate with fluid film lubrication and extremely low friction, and hence potentially negligible wear and a long implant life.

The design parameters for the construction of compliant layer bearings are known. Polyurethane elastomers have been the materials of choice for these bearings. Under conditions of cyclic loading and motion typical of the major load bearing joints in the human body there is much experimental evidence that this type of bearing will operate with extremely low friction, typical of fluid film lubrication. In contrast, Caravia et al (L. Caravia, D. Dowson and Fisher J., Start up and steady rate friction of thin polyurethane layers. Wear, (1993), 160, 191–197) cites that the use of compliant polyurethane layers in this application can result in unacceptably high friction values under conditions which combine heavy loading and low sliding velocities, i.e., at the onset of motion (start up friction).

SUMMARY OF THE INVENTION

The purpose of this invention is to address the important area of improving start up friction while maintaining effective fluid film lubrication during normal cyclic loading and motion.

The following definitions are used herein:

Ringers Solution: This is a material which comprises a sterile solution of sodium chloride, potassium chloride and calcium chloride in water. It contains in each 100 ml. not less than 323.0 mg and not more than 354.0 mg of sodium, not less than 14.9 mg and not more than 16.5 mg of potassium, not less than 8.20 mg and not more than 9.80 mg of calcium; and not less than 523.0 mg and not more than 580.0 mg of chloride.

Coefficient of friction ($\mu$): The ratio of tangential frictional force to the normal load for a plane surface.

Friction factor (f): The ratio of the product of frictional torque (T) and cup radius to the normal load for the cupped geometry considered in this study, during steady state motion.

Frictional torque (T): The torque required to resist rotation of the complaint layered cup about an axis perpendicular to the axis of loading, under the normal load and motion conditions.

Start up friction factor ($f_s$): Friction factor (f) at the onset of motion.

According to the present invention a process for improving start up and steady rate friction in an aqueous lubricant of soft/compliant polyurethanes includes treating a polyurethane element in Ringers solution, an aqueous solution of phosphate buffered saline or de-ionized water.

Preferably the process includes treating the element in a heated bath containing the respective aqueous solution at a constant temperature between 30° C. and 65° C., for example, good results have been obtained by treating the element at a temperature of 37° C. for 96 hours.

The invention also includes a polyurethane element which has been treated by the process set forth. The element can be or form part of a surgical or medical device which contacts body tissue and fluids, for example a prosthetic device, a stent, a catheter or an angio plastic balloon. The devices referred to above all operate with an aqueous lubricant provided by the synovial fluid in the human body.

As mentioned above, material treated by the process can be used as a bearing surface and thus a prosthetic device according to the invention can have a bearing surface at least part of which is formed from a polyurethane element which has been treated by the method set forth above.

The prosthetic device can have a first bearing surface formed from the treated material and a second cooperating surface formed from for example, metal or ceramic. The metal can be cobalt chrome steel, or similar metal or alloy used in implantable medical devices, and it can be provided with a diamond-like carbon (dlc) coating.

A diamond-like carbon coated metal prosthesis is disclosed in U.S. Pat. No. 5,593,452, the teachings of which are incorporated herein by reference.

When applied to, for example, a hip joint, the first treated surface can be provided on an acetabular cup and the second cooperating surface can be the cooperating ball head of the implant.

These and other objects and advantages of the present invention will become apparent from the following description of the accompanying drawings, which disclose several embodiments of the invention. It is to be understood that the drawings are to be used for the purposes of illustration only and not as a definition of the invention.

BRIEF DESCRIPTION OF THE DRAWINGS

In the drawings, wherein similar reference characters denote similar elements throughout the several views.

DESCRIPTION OF THE PREFERRED EMBODIMENT

The present invention addresses the issued of improving start up friction of compliant bearings designed for orthopedic applications and other uses while maintaining effective fluid film lubrication mechanism under normal cyclic loading and motion.

Figure 8:
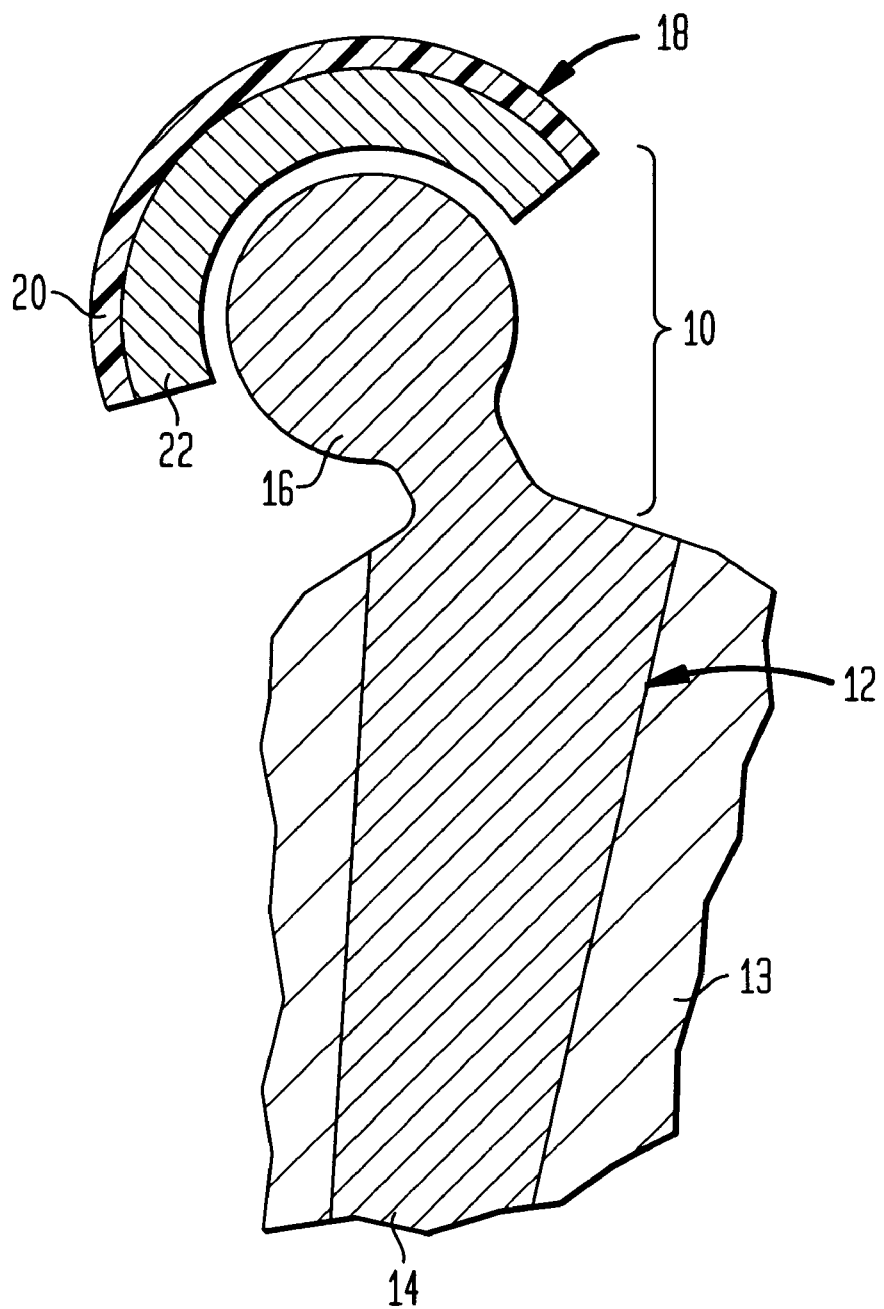
FIG. 8 is a cross-sectional view of a total hip joint in which the bearing of the present invention is utilized.

Referring to FIG. 8, there is shown an example prosthetic bearing which, in the example, is a total hip joint generally denoted as 10. The hip joint has a femoral component 12, implanted in a femur 13, with a stem 14 and a head 16. Head 16 engages an acetabular cup 18 which is composed of a metal or ceramic outer shell 20 and a soft or compliant bearing 22, which in the preferred embodiment, is polyurethane.

The evaluation of the friction properties of compliant layers referred to herein describes the properties of both "dry" contacts, and those lubricated with a low viscosity lubricant, i.e., pathological pseudo synovial fluid. The friction properties of the bearings have been measured on a machine that simulates the loads and motions experiences at the hip joint both at the start and during steady state motion.

In order to evaluate the invention, the process was applied to polyurethane acetabular cups and these were preconditioned under a variety of different aqueous buffer systems or de-ionized water. The acetabular cups were typically treated in a heated bath which contains a respective aqueous solution at a constant 37° C. for 96 hours. Further improvements can be realized by a shorter period at higher temperatures up to a maximum of 65° C. After this period the cups were removed, rinsed in de-ionized water, then cleaned by ultra-sonication for 15 minutes. The cups were then tested directly or sterilized by gamma irradiation. Post-treatment of the cups can be normally packaged and irradiated or a combination of these processes.

In order to provide a diamond-like carbon (dlc) coating on a femoral head element, a conventional 32 mm CoCr femoral head (manufactured by Howmedica) was treated using a commercial diamond-like carbon process, i.e., plasma assisted chemical vapor deposition (PA-CVD) to yield a coherent dlc coating over the articulating surface of the femoral head. The femoral head was used in the start up friction experiments described below, and as before provided an improvement in the start up friction in all cases;

(a) with the unconditioned compliant layer acetabular cup;

(b) after conditioning of complaint layer acetabular cup.

Frictional measurements (dry) were made with a simulator to measure the frictional torque developed in a hip joint under cyclic loads and motions typical of physiological conditions. The machine used is similar to that described by Unsworth, A. Dowson, D. Wright, V. (1974a) (The frictional behavior of human synovial joints—Part 1: Natural joints. Trans. ASME: J. Lub. Tech., 74-Lub-38). This apparatus is housed at Durham University, England. The apparatus consists of three main systems; which applied the joint load, drove the motion and measured the resulting frictional torque. The test hip joint was mounted with its center of rotation incident with the center of rotation of the simulator. The components were anatomically inverted, that is with the femoral head above the acetabular cup. A load of 1,000 N was used to protect the piezo electric transducer used in the simulator. Untreated (unmodified as manufactured) acetabular cups were used and the result is shown in Table 1 below.

TABLE 1

Dry Friction Factors of Common Counterfaces with Candidate Polyurethanes Compliant Layers

| Polyurethane Layer | CoCr Head | | Ceramic Head | |
|---|---|---|---|---|
| | Mean | s.d. | Mean | s.d. |
| CSIRO | 1.07 | 0.12 | 0.83 | 0.17 |
| Corethane | 1.01 | 0.18 | 1.02 | 0.13 |
| Chronoflex | 0.98 | 0.08 | 0.95 | 0.12 |
| Tecoflex | 0.88 | 0.13 | 0.94 | 0.14 |
| Tecothane | 0.77 | 0.30 | 0.93 | 0.17 |

The results showed that with typical polyurethane layers the dry friction factor values were typically 0.8 to 1.1. A friction factor of 1.0 would result in a frictional torque of approximately 30 Nm for an applied load of 2 kN acting to rotate a 32 mm diameter acetabular cup. This approached the value of 100 Nm, reported by Anderson et al., as the static torque required to dislodge a well fixed cemented prosthesis.

Consequently, should the bearings run dry or intimate contact between the bearing surfaces occur, the level of friction generated under these conditions with untreated compliant layer bearings would be sufficiently high to risk accelerated loosening and could result in early failure.

Frictional measurements with steady state lubrication using two different acetabular cups, cup 1 and cup 2, was then carried out.

Figure 1:
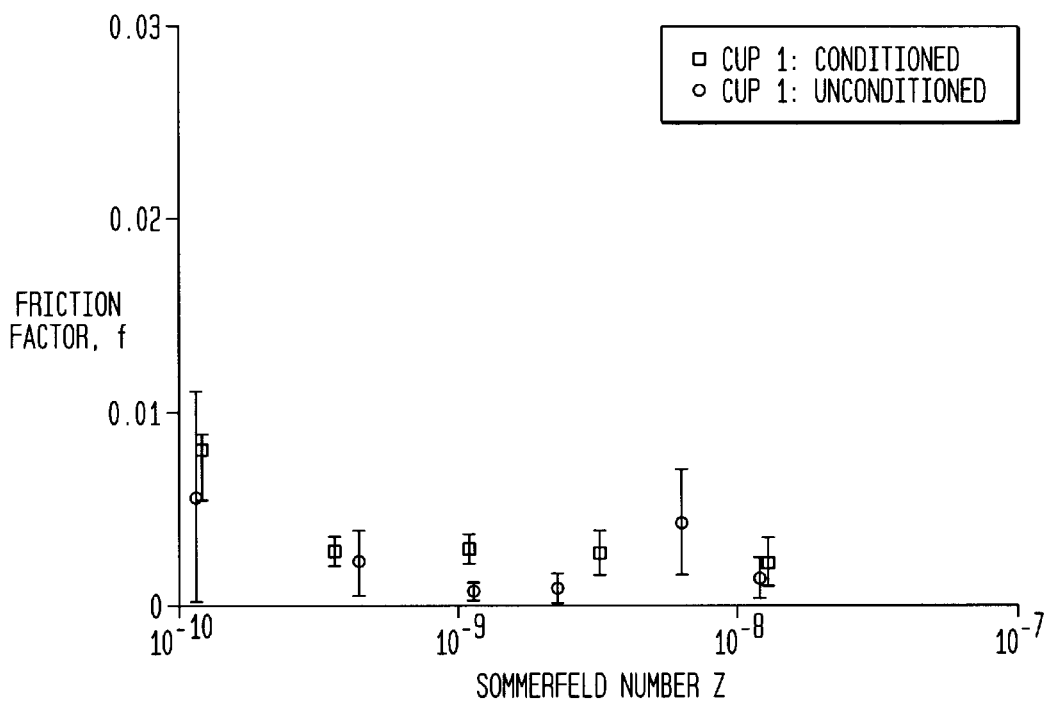
FIGS. 1 and 2 are graphs showing friction factors for two acetabular cups before and after treatment.
Figure 2:
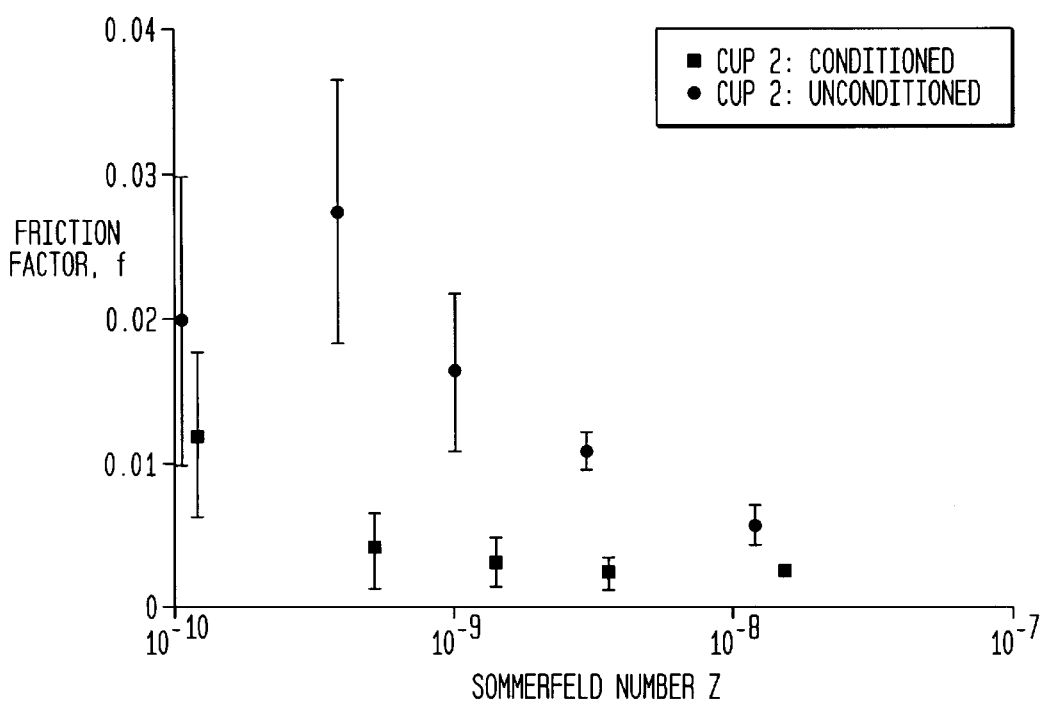

Steady state lubrication was assessed using two different acetabular cups, cup 1 and cup 2. Initially the cups were tested, after which the cups were conditioned in Ringers solution for 96 hours. Water based carboxyl methyl cellulose lubricants were used, with viscosities ranging from 0.001 Pas (distilled water) to 0.1 Pas. These fluids were chosen as they have similar rheological properties to synovial fluid. The steady state lubrication regime was assessed by conducting Stribeck analyses for each case; the results are given in FIGS. 1 and 2.

Conventional joints have friction factors which typically range from 0.05 with lubricant viscosities of 0.001 Pas, to 0.01 with lubricant viscosities of 0.1 Pas. Clearly both joints in the unconditioned state provide better lubrication with lower friction factors than conventional joints. Cup 1 exhibited extremely low friction factors through the range of lubrications used. The low friction factor values were at the lower limit of detection of the Durham hip function simulator. Conditioning cup 1 did not change its tribological performance; low friction factors were maintained. Cup 2 was manufactured to be tribologically inferior to cup 1, and so in the unconditioned state exhibits higher friction factors. However, the tribological performance of cup 2 was shown to improve considerably after conditioning, demonstrating clear advantages of the conditioning process for somewhat less than optimum bearings.

Figure 3:
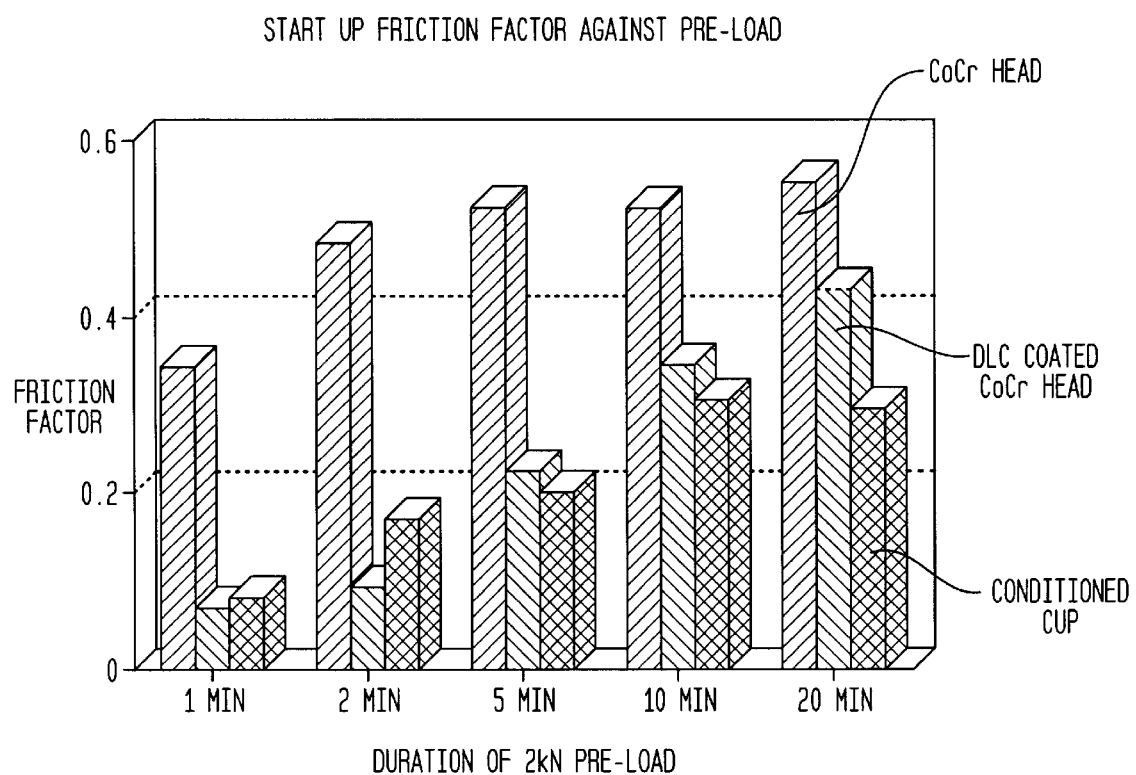
FIG. 3 is a diagram showing start up friction factor against preload time.

Frictional measurements for lubricated start-up friction were now carried out. During operation of the Durham hip function simulator, a preload of 2 kN was applied to mimic the effect of standing and loading an acetabular bearing without any flexion-extension motion. This was achieved by operating the simulator in the "reverse" loading mode. The "reverse" mode cycle started with a high load, and hence a delay in starting the motion enabled the test cups to experience a fixed preload of 2 kN for 1, 2, 5, 10 and 20 minutes. The frictional torque during the first tow cycles was measured, using water as the lubricant, for the head/cup combinations summarized in Table 2, and the results plotted against preload time in FIG. 3.

TABLE 2

Start-up Friction Factors

| Cup | Head | Start-up Factor at Different Durations of 2 kN Preload | | | | |
|---|---|---|---|---|---|---|
| | | 1 min | 2 min | 5 min | 10 min | 20 min |
| Unconditioned Cup | CoCr Head | 0.34 | 0.48 | 0.52 | 0.52 | 0.55 |
| Unconditioned Cup | DLC Coated CoCr Head | 0.07 | 0.09 | 0.22 | 0.34 | 0.43 |
| Conditioned Cup | CoCr Head | 0.06 | 0.16 | 0.20 | 0.23 | 0.43 |
| Conditioned Cup | DLC Coated CoCr Head | 0.08 | 0.17 | 0.20 | 0.30 | 0.29 |

Conditioning was conducted as described above.

In general the results show that as relative motion starts the frictional torque is high, but that this quickly reduces within one cycle, to the extremely low values expected from compliant layer bearings. There are two characteristics which have been used to differentiate between the material couples, that is the initial friction factors given in Table 2 and FIG. 3, and the rate at which the frictional torque decreases during the period of initial motion.

Figure 4:
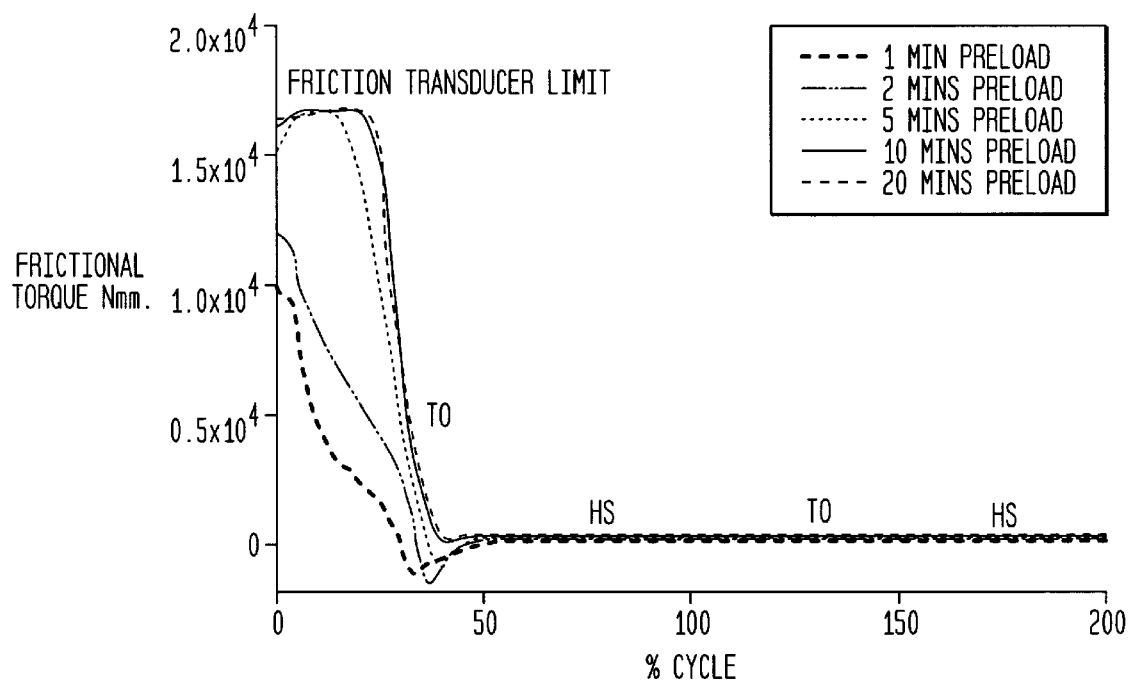
FIG. 4 is a graph showing start up friction for an unconditioned cup with CoCr head combination.
Figure 5:
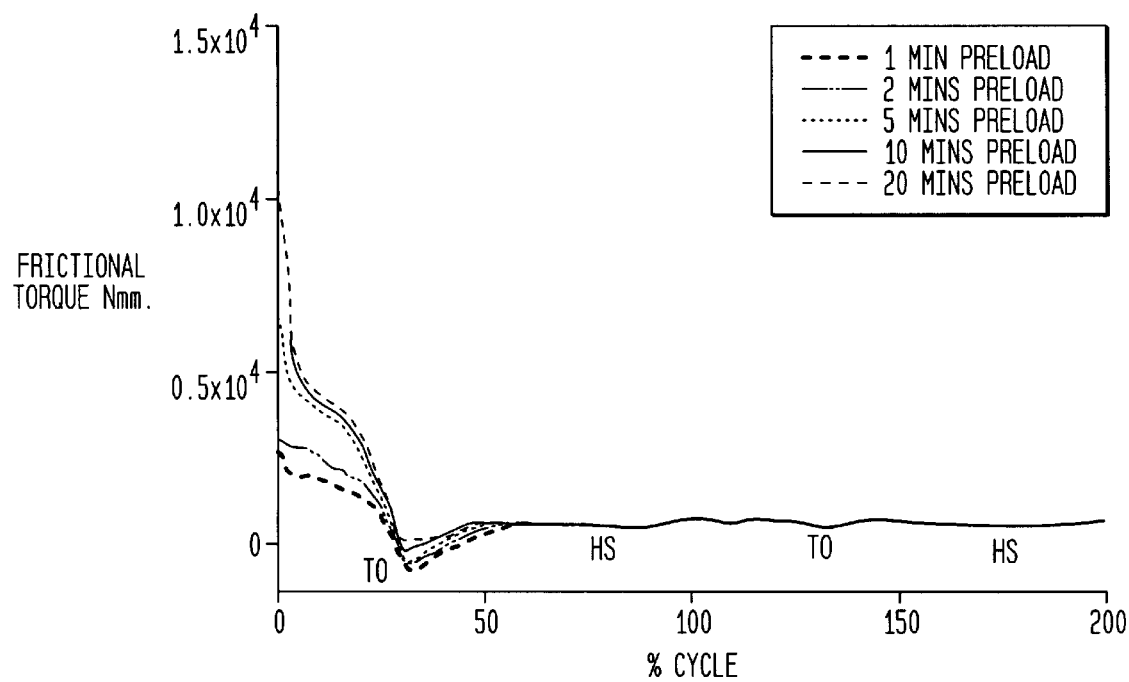
FIG. 5 is a graph showing start up friction for an unconditioned cup with a dlc head combination.

The unconditioned cup and cobalt chrome steel head develops very high frictional torque which remains high throughout the period of initial motion, FIG. 4. If a dlc coated head is used with the same unconditioned cup, then the initial frictional torque is lower (especially under shorter preload duration) FIG. 5, and it reduces still further as fluid is entrained during the stance phase.

Figure 6:
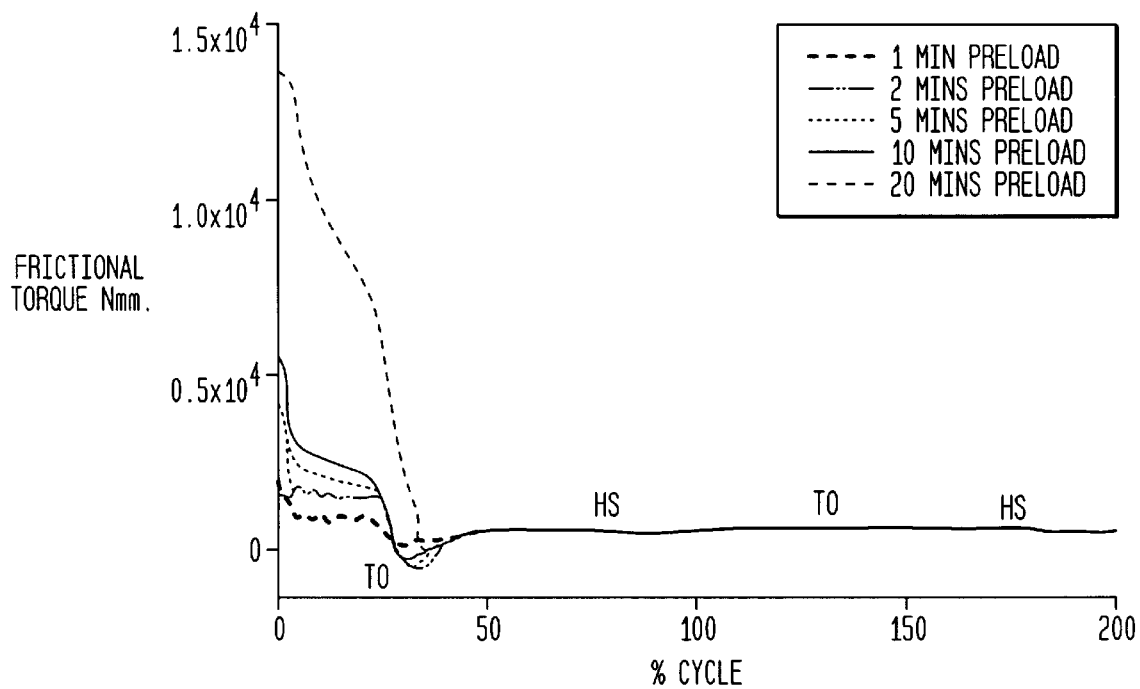
FIG. 6 is a graph showing start up friction for a conditioned cup with CoCr head combination.
Figure 7:
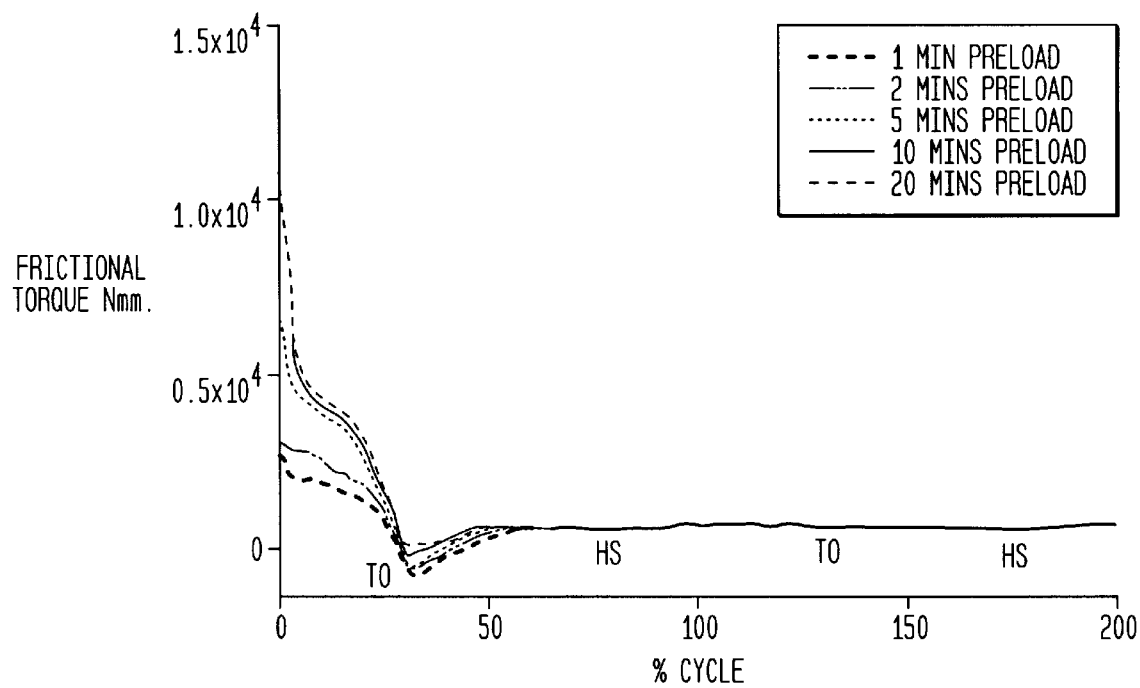
FIG. 7 is a graph showing start up friction for a conditioned cup with dlc head combinations.

The conditioned cup, FIGS. 6 and 7, develops initial frictional torque values to the unconditioned cup/dlc head combination. However, the frictional torque quickly reduces to a lower near constant value for the remainder of the cycle.

Caravia et al. assessed start-up friction developed between a thin polyurethane layer and several types of indenter using a pin on plate friction rig. A constant contact stress of 2 Mpa and a sliding velocity of 8 mms-1 was used. The indenter was loaded for between 5 s and 400 s and the peak friction measured using water as a lubricant. In contrast, this simulator experiment used a dynamically applied load with a maximum contact stress of 7.3 Mpa, a sinusoidal sliding velocity of maximum 34 mms$^{-1}$, and a preload of 2 kN applied for between 60 s and 1200 s.

Caravia et al. showed that the start-up friction increased with increasing preload time up to 80 s, after which they suggested the squeeze film action reached equilibrium and the friction increased no further. They reported higher values of start-up friction than this study, i.e., coefficients of friction between 0.6 and 1.1 for similar modulus material at 160 s preload. They also suggested that the surface energy of the bearing counter face could also be an important factor.

The experimental results of conditioned elements according to the present invention can be summarized:

1. Conditioning of the compliant layer cups provides for enhanced (or reduced) start up frictional performances and reduces the steady state friction.

2. Dlc coated head gives a slightly better performance than the uncoated head.

This work suggests that through the application of these inventions, either alone or in combination, leads directly to:

1) A significant reduction in start up friction.
2) A reduction in the effect of static preload on the frictional torque in the initial phase of motion.

These important results are critical to the long term performance of these bearings, since in contrast to the results presented by Caravia et al, which suggest start up friction may limit the life of such devices, these inventions significantly reduce this potential problem.

It was observed during the experiments described above that the effects of treating the compliant bearing acetabular cups in Ringers solution or phosphate buffered saline (PBS) or de-ionized water improved both the start up friction and the steady rate friction characteristics. The frictional changes were related to an effect of surface reorganization that occurs both within the bulk and at the surface of these polyurethane materials. These changes have been examined by the techniques of surface analysis such as ATR-fourier transforms infrared spectroscopy (ATR-FTIR), dynamic contact angle (DCA) and water uptake studies. Thus, the process to promote these beneficial changes was optimized.

These significant improvements in the start up and steady state friction have been achieved using the processes of the invention, either alone or in combination. The application of these developments is primarily targeted at bearing systems for joint or surface replacement involving, but not limited to the hip, knee, elbow, shoulder and ankle. The major purpose is to apply for example, conditioning to modify the surface chemistry of linear polyurethanes to attain a hydrophilic surface that has low contact angles and hence wets with aqueous lubricants. This method of surface modification can not only be applied to compliant layer joints but also other medical devices that contact body tissues and fluids, i.e., stents, catheters, angioplasty balloons, etc.

A further application is associated with reducing friction in mechanical systems where sliding contacts are involved, i.e., bushes (cylindrical or flat) that operates using predominantly aqueous lubricants.

While several examples of the present invention have been described, it is obvious that many changes and modifications may be made thereunto, without departing from the spirit and scope of the invention.

What is claimed is:

1. A prosthetic bearing having improved start up friction comprising:
   a first component with a metal or ceramic bearing surface;
   a second component with a compliant polyurethane bearing surface for sliding engagement with said first component, said polyurethane bearing surface having a surface reorganization resulting from treating the surface with an aqueous solution selected from the group consisting of Ringers solution, de-ionized water or a solution of phosphate buffered saline and a combination thereof at a temperature of 30° C. to 65° C.; and
   an aqueous lubricant for lubricating said first and second components.

2. The prosthetic bearing as set forth in claim 1 wherein the treatment with an aqueous solution is done at a temperature of 37° C. for 96 hours.

3. The prosthetic bearing as claimed in claim 1 wherein the polyurethane forms part of a surgical or medical device which contacts body tissues and fluids when in use.

4. The prosthetic bearing as claimed in claim 1 in which the metal is cobalt chrome.

5. The prosthetic bearing as claimed in claim 4 in which the metal bearing surface is provided with a diamond-like (dlc) coating.

6. The prosthetic bearing as claimed in claim 1 in which said second component bearing surface is provided on an acetabular cup and the first component bearing surface is a cooperating ball head of an implant.

7. The prosthetic bearing as set forth in claim 1 wherein the polyurethane is a polyurethane in which the surface chemistry is modified by said treatment with an aqueous solution to attain a hydrophilic surface that has low contact angles and wets with said aqueous lubricant.

8. A prosthetic bearing have improved start up friction comprising:
- a first component with a bearing surface;
- a second component with a compliant polyurethane bearing for sliding engagement with said first component, said polyurethane bearing surface formed of a polyurethane having a surface chemistry modified by conditioning at least the bearing surface with an aqueous solution to attain a hydrophilic surface that has a low contact angle.

9. The prosthetic bearing as set forth in claim 8 wherein an aqueous lubricating solution is provided for lubricating said first and second components.

10. The prosthetic bearing as set forth in claim 8 wherein the aqueous solution is selected from the group consisting of Ringers solution, de-ionized water or a solution of phosphate buffered saline and a combination thereof.

11. The prosthetic bearing as set forth in claim 10 wherein said conditioning with said aqueous solution is done at a temperature of 37° C. to 65° C.

12. The prosthetic bearing as set forth in claim 11 wherein the treatment with an aqueous solution is done at a temperature of 37° C. for 96 hours.

13. The prosthetic bearing as claimed in claim 8 wherein the polyurethane forms part of a surgical or medical device which contacts body tissues and fluids when in use.

14. The prosthetic bearing as claimed in claim 13 wherein the second component is a prosthetic device, a stent, a catheter or an angio-plastic balloon.

15. The prosthetic bearing as claimed in claim 8 in which the first component is metal or ceramic.

16. The prosthetic bearing as claimed in claim 15 in which the metal bearing surface is provided with a diamond-like (dlc) coating.

17. The prosthetic bearing as claimed in claim 8 in which said second component bearing surface is provided on an acetabular cup and the first component surface is a cooperating ball head of an implant.

* * * * *